(12) United States Patent
Bartoszyk et al.

(10) Patent No.: US 7,928,128 B2
(45) Date of Patent: *Apr. 19, 2011

(54) USE OF (R)-(−)-2-[5-(4-FLUOROPHENYL)-3-PYRIDYLMETHYLAMINOMETHYL]-CHROMANE AND ITS PHYSIOLOGICALLY ACCEPTABLE SALTS

(75) Inventors: Gerd Bartoszyk, Weiterstadt (DE); Hermann Russ, Darmstadt (DE); Christoph Seyfried, Seeheim-Jugenheim (DE); Frank Weber, Gross-Zimmern (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 696 days.

This patent is subject to a terminal disclaimer.

(21) Appl. No.: 10/221,031

(22) PCT Filed: Feb. 1, 2001

(86) PCT No.: PCT/EP01/01038
§ 371 (c)(1),
(2), (4) Date: Dec. 30, 2002

(87) PCT Pub. No.: WO01/68063
PCT Pub. Date: Sep. 20, 2001

(65) Prior Publication Data
US 2003/0181486 A1    Sep. 25, 2003

(30) Foreign Application Priority Data
Mar. 10, 2000 (EP) .................................. 00104531

(51) Int. Cl.
*A61K 31/44* (2006.01)
*A61K 31/35* (2006.01)
(52) U.S. Cl. .................... 514/337; 514/456; 514/444
(58) Field of Classification Search .................. 514/337, 514/456, 444
See application file for complete search history.

(56) References Cited

U.S. PATENT DOCUMENTS

| | | | |
|---|---|---|---|
| 4,438,119 A * | 3/1984 | Allen et al. | 514/252.15 |
| 4,981,695 A * | 1/1991 | Appelgren et al. | 424/456 |
| 5,137,901 A | 8/1992 | Junge et al. | |
| 5,141,930 A | 8/1992 | Nakao | |
| 5,314,888 A | 5/1994 | Dodman et al. | |
| 5,318,988 A | 6/1994 | Schohe-Loop et al. | |
| 5,468,882 A | 11/1995 | Schohe-Loop et al. | |
| 5,502,080 A * | 3/1996 | Hitzig | 514/654 |
| 5,541,199 A | 7/1996 | Mewshaw et al. | |
| 5,670,667 A | 9/1997 | Mewshaw et al. | |
| 5,756,521 A | 5/1998 | Mewshaw et al. | |
| 5,762,960 A | 6/1998 | Dodman | |
| 5,767,132 A | 6/1998 | Boettcher et al. | |
| 5,935,973 A | 8/1999 | Birch et al. | |
| 6,114,334 A | 9/2000 | Kerrigan et al. | |
| 6,214,829 B1 | 4/2001 | Feenstra et al. | |
| 6,235,774 B1 | 5/2001 | Fahrig et al. | |
| 6,242,456 B1 | 6/2001 | Dodman et al. | |
| 2003/0181486 A1 | 9/2003 | Bartoszyk et al. | |

FOREIGN PATENT DOCUMENTS

| | | |
|---|---|---|
| DE | 2364685 | 7/1975 |
| DE | 4135474 | 4/1993 |
| DE | 4226527 | 2/1994 |
| DE | 196 48 384 | 5/1998 |
| DE | 19648384 | 5/1998 |
| EP | 0145067 | 6/1985 |
| EP | 0465254 | 1/1992 |
| EP | 0 707 007 | 4/1996 |
| EP | 0707007 | 4/1996 |
| EP | 0900792 | 3/1999 |
| WO | WO 93/17670 | 9/1993 |
| WO | WO 9317017 | 9/1993 |
| WO | WO 9418196 | 8/1994 |
| WO | WO 9533729 | 12/1995 |
| WO | WO 9703071 | 1/1997 |
| WO | WO 9945906 | 9/1999 |
| WO | WO 0029397 | 5/2000 |

OTHER PUBLICATIONS

The Merck Manual of Diagnosis and Therapy, Seventeenth Edition, 1999.*
Bonifati V et al: "Buspirone in Levodopa-Induced Dyskinesias" Clinical Neuropharmacology, Raven Press, New York, NY, US, vol. 17, No. 1, 1994, pp. 73-82, XP001087558 ISSN: 0362-5664.
English Abstract of DE 196 48 384.
Luescher et al., Stereotypic or Obsessive-Compulsive Disorders in Dogs and Cats, 1991, Veterinary Clinics of North America. Small Animal Practice, 21(2), pp. 401-413.
Bartoszyk et al., Pharmacological Profile of EMD 128130: A Putative Atypical Antipsychotic with DA D2 Antagoinistic and Serotonin 5-HT1A Agonistic Properties, 1997, Soc. Neurosci. Abstr., 23, p. 530 (#207.5).
Bottcher et al., SAR for Novel Chromanes: Atypical Neuroleptics with 5HT1A Agonistic and D2 Antagonistic Activity, 1996, Soc. Neurosci. Abstr., 22, p. 841 (#334.1).
Brotchie et al., Levodopa-induced dyskinesia in Parkinson's disease, Journal of Neural Transmission, J Neural Transm (2005) 112: 359-391.
Seyfried et al., Biochemical and functional studies on EMD 49 980: a potent, selectively presynaptic D-2 dopamine agonist with actions on serotonin systems, European Journal of Pharmacology, 160 (1989) 31-41.
Hofmeyr, J.M.: The use of haloperidol as a long-acting neuroleptic in game capture operations, J.S. Afr. Vet. Assoc. 52:273-282, 1981. Pub Med ID 7857027, 1994.
Overall K L, "Animal Behavior Case of the Month," Journal of the American Veterinary Medical Association, XX, XX, Sep. 1, 1994, pp. 694-696, vol. 5, No. 205, XP008001693, ISSN: 0003-1488, cited in the application, p. 495, right-hand column, paragraphs 2,3.

(Continued)

*Primary Examiner* — Sreeni Padmanabhan
*Assistant Examiner* — Shobha Kantamneni
(74) *Attorney, Agent, or Firm* — Millen, White, Zelano & Branigan, P.C.

(57) ABSTRACT

(R)-(−)-2-[5-(4-fluorophenyl)-3-pyridylmethylaminomethyl]-chromane or a physiologically acceptable salt thereof is useful for treatment of adverse effects in treating Parkinson's disease.

7 Claims, No Drawings

OTHER PUBLICATIONS

Griebel G. et al., "5-HT1A Agonists Modulate Mouse Antipredator Defensive Behavior Differently from the 5-HT2A Antagonist Pirenperone," Pharmacol. Biochem. Behav., 1995, pp. 235-244, vol. 51, No. 2-3, XP002197804, cited in the application, p. 242, p. 241, right-hand column, paragraph 1-paragraph 3, p. 241, left-hand column, last paragraph, p. 236, left-hand column, paragraph 2.

Bartoszyk G D et al., "Pharmacological Profile of EMD 128130: A Putative Atypical Antipsychotic with Dopamine D2 Antagonistic and Serotonin 5-HT1A Angonistic Properties," Society for Neuroscience Abstracts, Oct. 25, 1997, p. 530, vol. 23, No. 1/2, XP001066595, ISSN: 0190-5295, abstract 207.5, Society for Neuroscience, US.

Schlemmer R F et al., "Antagonism of Amphetamine-induced Behavior by the Antipshychotic Candidate EMD 77697 in a Primate Social Colony Model for Screening Antipsychotic Agents," Society for Neuroscience Abstracts, Oct. 25, 1997, p. 1931, vol. 23, No. 1/2, XP001066577, ISSN: 0190-5295; abstract 747.18, Society for Neuroscience, US.

Vliet Van B J et al., "Preclinical Pharmacology of SLV301, a Potent Dopamine D2 Receptor Antagonist and Selective Serotonin Reuptake Inhibitor," Society for Neuroscience Abstracts, Nov. 4-9, 2000, p. 87116, vol. 26, No. 1/2, XP008001595, ISSN: 0190-5295, abstract, Society for Neuroscience, US.

Liu Y et al., "Derivatives of CIS-2-amino-8-hyroxy-1-Methyltetralin: Mixed 5-HT1A-Receptor Agonists and Dopamine D2-receptor Antagonists," Journal of Medicinal Chemistry, 1995, pp. 150-160, vol. 1, No. 38, XP001064450, ISSN: 0022-2623, the whole document, American Chemical society, Washington, US.

Joechle W, Fehlverhalten Und Anpassungsprobleme Bei Hund Und Katze Und Deren Pharmakologische Beeinflussbarkeit//Abnormal Behavior and Adaptation Problems and their Pharmacological Control in Dogs and Cats, Tieraerztliche Praxis, Nov. 1998, pp. 410-421, vol. 6, No. 26, XP008001694, ISSN: 0303-6286, the whole document, Schattauer, DE.

Database Biosis 'Online!, Biosciences Information Service, STN AN= 1995:131485, XP002197805, Abstract, Philadelphia, PA, US; & Molewijk et al., "Conditioned ultrasonic distress vocalizations in adult male rats as a behavioral paradigm for screening antipanic drugs," Psychopharmacology, 1995, pp. 32-40, vol. 117, No. 1, abstract.

Database Drugnl 'Online!, STN AN=97:3859, XP002197806, abstract, & R&D Focus Drug News, Mar. 11, 1997, abstract.

Kleven M et al., "Role of 5-HT1A Receptors in the Ability of Mixed 5-HT1A Receptor Agonist/Dopamine D2 Receptor Antagonists to Inhibit Methylphenidate-induced Behaviors in Rats," European Journal of Pharmacology, Oct. 10, 1996, pp. 25-34, vol. 313, No. 1/2, XP001066337, ISSN: 0014-2999, Abstract, Amsterdam, NL, p. 26, left-hand column -right-hand column, paragraph 1, p. 29-p. 32.

Prog Neuropsychopharmacol Biol Psychiat (in press), The Effect of Chronic Administration of Sarizotan, 5-HT1Agonist/D3/4 Ligand on Haloperidol Induced Repetitive Jaw Movements in Rat Model of Tardive Dyskinesia, Helen Rosengarten et al., pp. 1-21.

Research Article—Effects of serotonin 5-HT1A agonist in advanced Parkinson's disease, William Bara-Jimenez et al., pp. 1-5.

Psychopharmacology © Springer-Verlag 2005—Changes in sleep electroencephalogram and nocturnal hormone secretion after administration of the antidyskinetic agent sarizotan in healthy young male volunteers, Heike E. Kuenzel et al., pp. 1-11.

Journal of Psychopharmacology—16(3) (2002) 195-199—Evaluation of EMD 128 130 occupancy of the 5-HT$_{1A}$ and the D$_2$ receptor: a human PET study with [$^{11}$C]WAY-100635 and [$^{11}$C]raclopride, Eugenii A. Rabiner et al., pp. 195-199.

Clin Neuropharmacol—vol. 27, No. 2, Mar.-Apr. 2004, Multicenter, Open-Label, Trial of Sarizotan in Parkinson Disease Patients WIth Levodopa-Induced Dyskinesias (the SPLENDID Study), C. Warren Olanow et al., pp. 58-62.

J Neural Transm (2004) 111: 113-126— Sarizotan, a serotonin 5-HT$_{1A}$ receptor agonist and dopamine receptor ligand. 1. Neurochemcial profile, G. D. Bartoszyk et al., pp. 113-126.

Neuropharmacology 45 (2003) 1057-1069—Contribution of the serotonin 5-HT$_{1A}$ receptor agonism of 8-OH-DPAT and EMD 128130 to the regulation of haloperidol-induced muscle rigidity in rats. E.Lorenc-Koci et al., pp. 1057-1069.

Soc. Neurosci. Abstr., vol. 23, Part 1, p. 530, 1997—209.5 Pharmacological Profile of EMD 128130: A Putative Atypical Antipsychotic With Dopamine D$_2$ Antagonistic and Serotonin 5-HT$_{1A}$ Agonistic Properties, G.D. Banoezyk et al.

Soc. Neurosci. Abstr., vol. 22, Part 2, p. 841, 1996, 234.1—SAR for Novel Chromanes: Atypical Neuroleptics With 5HT1A Agonistic and D2 Antagonistic Activity, H. Bottcher et al.

Neurology 57 Nov. (2 of 2) 2001—Serotonin 5-HT1A agonist improves motor complications in rodent and primate parkinsonian models, Francesco Bibbiani et al., pp. 1829-1834.

Hirose et al., Chem. Pharm. Bull., 24(11):2661-2667 (1976).

Goldenberg et al., Chimie Therapeutique. 8(3):259-270 (May/Jun. 1973).

Chem. Abstracts, 70(7):28816q (Feb. 17, 1969).

Chem. Abstracts, 94(13):103390x (Mar. 30, 1981).

Fujikura et al., Chem. Pharm. Bull., 30(11):4092-4101 (1982).

Chem. Abstracts, 86(21):150434j (May 23, 1977).

Chem. Abstracts, 72(21):109472t (May 25, 1970).

Patent Abstracts of Japan, vol. 18, No. 19 (C-1152 (Jan. 13, 1994) JP-A-05 255 302 (Yamanouchi Pharmaceutical Co., Ltd.) Oct. 5, 1993 and computer translation of document.

Mewshaw R E et al.: "New Generation Dopaminergic Agents. 1. Discovery of a Novel Scaffold Which Embraces the D2 Agonist Pharmacophore. Structure-Activity Relationship of a Series of 2-(Aminomethyl)chromans" Journal of Medicinal Chemistry American Chemical Society. Washingotn, US vol. 40, No. 26, 1997, pp. 4235-4256, XP002155829.

Bonifati V et al: "Buspirone in Levodopa-Induced Dyskinesias" Clinical Neuropharmacology, Raven Press, New York, NY, US, vol. 17, No. 1, 1994, pp. 73-82, XP001087558.

Blanchet P J et al: "Dopa-Induced "Peak Doses" Dyskinesia: Clues Implicating D2 Receptor-Mediated Mechanisms Using Dopaminergic Agonists in MPTP Monkeys."Journal of Neural Transmission. Supplementim. Austria 1995, vol. 45, 1995, pp. 103-112, XP008016069.

Berkow R et al: "The Merck Manual—128. Disorders of Movement: Extrapyramidal and Cerebellar Disorders" Merck Manual of Diagnosis and Therapy Rahway, Merck Research Laboratories, US, 1992, pp. 1491-1503, XP002223982.

Copending U.S. Appl. No. 10/484,697 "Novel Use of 2-[5-(4-Fluorophenyl)-3-Pyridylmethylaminomethyl]-Chromane and Its Physiologically Acceptable Salts" Gerd Bartoszyk et al., pages.

* cited by examiner

USE OF (R)-(−)-2-[5-(4-FLUOROPHENYL)-3-PYRIDYLMETHYLAMINOMETHYL]-CHROMANE AND ITS PHYSIOLOGICALLY ACCEPTABLE SALTS

The present invention relates to the use of (R)-(−)-2-[5-(4-fluorophenyl)-3-pyridylmethylaminomethyl]-chromane or a physiologically acceptable salt thereof, for the manufacture of a medicament for the treatment of extrapyramidal movement disorders and/or for the manufacture of a medicament for the treatment of adverse effects of anti-Parkinsonian drugs in extrapyramidal movement disorders and/or for the manufacture of a medicament for the treatment of extrapyramidal symptoms (EPS) induced by neuroleptics.

(R)-(−)-2-[5-(4-fluorophenyl)-3-pyridylmethylaminomethyl]-chromane, physiologically acceptable salts thereof (U.S. Pat. No. 5,767,132, column 9, lines 6 to 32) and a process (U.S. Pat. No. 5,767,132, Example 19) by which it/they can be prepared are known from U.S. Pat. No. 5,767,132. The compound which is referred to herein is described in the patent as a combined selective dopamine $D_2$ receptor antagonist and 5-$HT_{1A}$ receptor agonist. Therefore, the use of (R)-(−)-2-[5-(4-fluorophenyl)-3-pyridylmethylaminomethyl]-chromane and its physiologically acceptable acid addition salts for the manufacture of a medicament for prophylaxis and control of the sequelae of cerebral infarction (apoplexia cerebri) such as stroke and cerebral ischaemia, for prophylaxis and control of cerebral disorders, e.g. migraine, especially in geriatrics in a manner similar to certain ergot alkaloids, the treatment of anxiety, tension and depression states, sexual dysfunctions caused by the central nervous system, for disturbances in sleep or absorption of food or for the treatment of psychosis (schizophrenia) is disclosed.

Additionally, they are suitable to eliminate cognitive deficiencies, to improve powers of learning and memory and to treat Alzheimer's disease. They can be furthermore used for treating side-effects in the treatment of hypertension, in endocrinology and gynecology, e.g. for the treatment of acromegaly, hypogonadism, secondary amenorrhea, premenstrual syndrome or undesired puerperal lactation.

The invention had the object of providing novel uses for (R)-(−)-2-[5-(4-fluorophenyl)-3-pyridylmethylaminomethyl]-chromane and its physiologically acceptable salts.

It is hereby disclosed that (R)-(−)-2-[5-(4-fluorophenyl)-3-pyridylmethylaminomethyl]-chromane and its physiologically acceptable salts have significantly better pharmacological properties than compounds of the prior art.

It has been found that (R)-(−)-2-[5-(4-fluorophenyl)-3-pyridylmethylaminomethyl]-chromane or physiologically acceptable salts also have therapeutic activity against extrapyramidal movement disorders such as idiopathic Parkinsons's disease, Parkinson syndromes, dyskinetic, choreatic, or dystonic syndromes, tremor, Gilles de la Torette syndrome, ballism, myoclonus, restless legs syndrome or Wilsons's disease, as well as extrapyramidal motoric disturbances [synonymous extrapyramidal symptoms (EPS)] induced by neuroleptics.

Additionally it has been found that (R)-(−)-2-[5-(4-fluorophenyl)-3-pyridylmethyl-aminomethyl]-chromane or physiologically acceptable salts have therapeutic activity against adverse effects of anti-Parkinsonian drugs in extramyramidal movement disorders, in particular against dopaminomimetic adverse effects of anti-Parkinsonian drugs in idiopathic Parkinson's disease or Parkinson syndromes.

Furthermore it has been found that (R)-(−)-2-[5-(4-fluorophenyl)-3-pyridylmethyl-aminomethyl]-chromane or physiologically acceptable salts show an extremely low liability to induce extrapyramidal side effects. Extrapyramidal motor side effects in e.g. rodents are measured by the ability of a drug to induce catalepsy. Catalepsy is defined as a state where an animal continues to remain in an unnormal (nonphysiological 'uncomfortable') posture for a long time (e.g.: M. E. Stanley and S. D. Glick, Neuropharmacology, 1996; 15: 393-394; C. J. E. Niemegeers and P. Janssen, Life Sci., 1979, 201-2216). For example, if a hindpaw of a rat is placed on an elevated level, e.g. a platform elevated 3 cm above ground level, a normal rat immediately withdraws the hindpaw from the platform to the ground level. A cataleptic rat remains in this unnatural posture even for minutes.

Although (R)-(−)-2-[5-(4-fluorophenyl)-3-pyridylmethyl-aminomethyl]-chromane or physiologically acceptable salts have a dopamine antagonistic mechanism of action which is known to induce extrapyramidal motor side effects (C. J. E. Niemegeers and P. Janssen, Life Sci., 1979, 201-2216), unexpectedly (R)-(−)-2-[5-(4-fluorophenyl)-3-pyridylmethyl-aminomethyl]-chromane does not induce any catalepsy in rats in doses up to 500 fold higher compared to the doses effective in the animal models indicative for the before-mentioned therapeutic indications.

Even more unexpectedly, (R)-(−)-2-[5-(4-fluorophenyl)-3-pyridylmethylaminomethyl]-chromane or physiologically acceptable salts moreover are able to prevent catalepsy induced by conventional antidopaminergic drugs and even reverses already existing catalepsy induced by conventional antidopaminergic drugs such as haloperidol; the doses for this anticataleptic effect are in the same dose-range shown to be effective in the animal models indicative for the before-mentioned therapeutic indications.

Beneficial effects on the extrapyramidal motoric system have previously been described for other drugs with 5-$HT_{1A}$ agonistic action. Buspirone for example, which is an anxiolytic drug by nature, exhibits moderate anti-dyskinetic properties in advanced Parkinson patients (B. Kleedorfer et al., J Neurol Neurosurg Psychiatry, 1991, 54: 376-377; V. Bonifati et al., Clin Neuropharmacol, 1994, 17: 73-82). The main mechanism of action is obviously via stimulation of 5-$HT_{1A}$ receptors of the raphe nigral and raphe striatal pathways. In contrast to buspirone, (R)-(−)-2-[5-(4-fluorophenyl)-3-pyridylmethyl-aminomethyl]-chromane and the physiologically acceptable salts thereof are by far (30-fold) more potent agonists at the 5-$HT_{1A}$ receptor with an $IC_{50}$ of 1 nmol/l ($IC_{50}$ of buspirone: 30 nmol/l).

Furthermore, (R)-(−)-2-[5-(4-fluorophenyl)-3-pyridylmethyl-aminomethyl]-chromane and the physiologically acceptable salts thereof exhibit a $D_2$ antagonism under increased doses which represents an additional advantage in comparison to conventional 5-$HT_{1A}$ agonists like buspirone. On one hand, the $D_2$ antagonism lowers the risk of psychotic reactions caused by the stimulation of serotonin receptors and, on the other hand, emphasises indirectly the $D_1$ properties of the co-administered nonselective $D_1/D_2$ agonist l-dopa. A more selective stimulation of $D_1$ receptors is known to be beneficial for the treatment of dyskinesias in Parkinson's disease (P. J. Blanchet et al., J Neural Transm, 1995, 45 (Suppl.): 103-112). Therefore both, the 5-$HT_{1A}$ agonistic and the $D_2$ antagonistic properties of (R)-(−)-2-[5-(4-fluorophenyl)-3-pyridylmethyl-aminomethyl]-chromane or a physiologically acceptable salt thereof, contribute to the advantageous effects on the extrapyramidal motoric system.

The pharmacological profile of (R)-(−)-2-[5-(4-fluorophenyl)-3-pyridylmethylaminomethyl]-chromane and its physiologically acceptable salts is furthermore characterized by a high affinity to the dopamine $D_3$ receptor. The $D_3$ receptor is obviously involved in the pathogenesis of dyskinesia. So an association between a genetic polymorphism of the dopamine $D_3$ receptor and the disposition to develop tardive dyskinesia has recently been reported (Segmann et al. 1999, Mol-Psychiatry 4: 247). Additionally, there is obviously an increased density of dopamine $D_3$ receptors in Parkinson patients with l-dopa-induced dyskinesia. Therefore, the interaction of (R)-(−)-2-[5-(4-fluorophenyl)-3-pyridylmethyl-aminomethyl]-chromane or one of its physiologically acceptable salts with the dopamine $D_3$ receptor is an additional important mechanism leading to beneficial effects on the extrapyramidal system, in particular in the treatment of dyskinesia.

The a typical neuroleptic clozapine is regarding the extrapyramidal effects—but not regarding structure or side effects—congruent with (R)-(−)-2-[5-(4-fluorophenyl)-3-pyridylmethyl-aminomethyl]-chromane or a physiologically acceptable salt thereof particularly in scope of the anticataleptic properties. Recent studies provide evidence that clozapine ameliorates dyskinesias in Parkinson's disease (F. Perelli et al., Acta Neurol Scan, 1998, 97: 295-299; P. Pollak et al., Lancet, 1999, 353: 2041-2041). Besides that, clozapine is known to have a variety of other beneficial effects on extrapyramidal movement disorders, like in tardive dyskinesia, tremor, Huntington's disease, Tourette's syndrome, akathisia and dopaminomimetic psychosis (C. Pfeiffer and M. L. Wagner, Am J Hosp Pharm, 1994, 51: 3047-3053). (R)-(−)-2-[5-(4-fluorophenyl)-3-pyridylmethyl-aminomethyl]-chromane or a physiologically acceptable salt improve these kinds of movement disorders even without bearing the risk of the fatal side effects of clozapine like agranulocytosis and acute nephritis (J. Alvir et al., N Engl J Med, 1993, 329: 162-167; T. J. Elias et al., Lancet, 1999, 354: 1180-1181).

Therefore, the present invention relates to the use of (R)-(−)-2-[5-(4-fluorophenyl)-3-pyridylmethylaminomethyl]-chromane or a physiologically acceptable salt thereof, for the manufacture of a medicament for the treatment of extrapyramidal movement disorders.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore, the invention relates to the use for the manufacture of a medicament for the treatment of extrapyramidal movement disorders in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of extrapyramidal movement disorders.

(R)-(−)-2-[5-(4-fluorophenyl)-3-pyridylmethyl-aminomethyl]-chromane or a physiologically acceptable salt, useful for the treatment of extrapyramidal movement disorders, in particular for the treatment of idiopathic Parkinson's disease, Parkinson syndromes, dyskinetic, choreatic or dystonic syndromes, extrapyramidal motoric adverse effects of neuroleptics, tremor, Gilles de la Tourette syndrome, ballism, myoclonus, restless legs syndrome or Wilson's disease and/or useful for the treatment of adverse effects in idiopathic Parkinson's disease or Parkinson syndromes including medicinal compositions as defined below, is preferably administered in doses from 0.1 to 100 mg, preferentially between approximately 1 and 20 mg. The composition may be administered once or more times a day, e.g. 2, 3, or 4 times daily. The specific dose for each patient depends on all sorts of factors, e.g. on the activity of the specific compound employed, on the age, body weight, general state of health, on sex, diet, time and route of administration, on the excretion rate, pharmaceutical substance combination and on the severity of the particular disorder to which the therapy relates. Oral administration is preferred, but also parenteral routes of administration (e.g. intravenous or transdermal) can be utilized.

Anti-Parkinsonian drugs are conventional drugs such as l-dopa (levodopa) and l-dopa combined with benserazide or carbidopa, dopamine agonists such as bromocriptine, apomorphine, cabergoline, pramipexol, ropinirol, pergolide, dihydro-α-ergocriptine or lisuride plus all drugs acting via stimulation of dopamine receptors, inhibitors of catechol-O-methyl transferase (COMT) such as entacapone or tolcapone, inhibitors of monoamine oxidase (MAO) such as selegiline and antagonists of N-methyl-D-aspartate (NMDA) receptors such as amantadine or budipine.

Adverse effects of said anti-Parkinsonian drugs are all types of dyskinesias, such as choreic, dystonic, ballistic and myoclonic dyskinesia, as well as motor (response) fluctuations or psychotic states.

Therefore, the present invention relates to the use of (R)-(−)-2-[5-(4-fluorophenyl)-3-pyridylmethylaminomethyl]-chromane or a physiologically acceptable salt thereof, for the manufacture of a medicament for the treatment of adverse effects of anti-Parkinsonian drugs in idiopathic Parkinson's disease.

Treatment of adverse effects of conventional anti-Parkinsonian drugs as defined above are determined in a modification of the animal model of the Parkinsonian cynomolgus monkey according to P. J. Blanchet et al., Exp. Neurology 1998; 153: 214-222. Monkeys render parkinsonian by repeated injections of 1-methyl-4-phenyl-1,2,3,6-tetrahydropyridine (MPTP). The Parkinsonian monkeys are chronically treated with the standard l-dopa therapy according to P. J. Blanchet et al., Mov. Disord., 1998; 13: 798-802. Longterm treatment with l-dopa induces extrapyramidal motor side effects and psychotic states which are both qualitatively and quantitatively, assessed by the Abnormal Involuntary Movement Scale (P. J. Blanchet et al., Mov. Disord. 1998; 13: 798-802) for different body parts (face, neck, trunk, each limb) and by rating for psychotic states by observing the monkey's attention, reactivity and mobility. (R)-(−)-2-[5-(4-fluorophenyl)-3-pyridylmethylaminomethyl]-chromane reduced overall choreiform dyskinesias and dystonic dyskinesias as well as psychotic states.

A typical study to investigate the efficacy of the compounds according to the invention for adverse effects in Parkinson's disease is described in the following. 40 patients of either sex with advanced idiopathic Parkinson's disease complicated by "peak-dose" dyskinesia participate in a double-blind, cross-over study. The main inclusion criteria are Hoehn & Yahr stage ≧2.5 (lit.: Hoehn H. M. et al, Neurology 1967; 17: 427-442), aged 40-75 years, symptom duration of at least 5 years, and a l-dopa treatment duration of at least 3 years. (R)-(−)-2-[5-(4-fluorophenyl)-3-pyridylmethylaminomethyl]-chromane hydrochloride or placebo is administered as "add on" to the conventional Parkinson treatment, which is maintained unchanged during the whole study. The dose of blinded medication is titrated over a period of 3 weeks in a range from 2.5 to 10 mg b.i.d. Then the medication is kept constant for 1 week. Before the start of titration and at the end of the treatment period a l-dopa challenge is performed according to P. Damier et al. (Movement Disord, 1999, 14 (Suppl. 1), 54-59) using video recording. The main outcome measure of the protocol is the mean score for dyskinesia during the first hour in the "on" state after l-dopa challenge.

Therefore, the investigator assesses every minute the severity of dyskinesia (0=absent, 4=severe disabling involuntary movements) from 0 to 4 in seven parts of the body (upper and lower limbs, face, trunk, neck). After a 2-week wash-out period the two study arms are crossed over and the protocol is repeated. The statistical analysis of the mean dyskinesia scores demonstrates a significant clinical improvement under treatment with (R)-(−)-2-[5-(4-fluorophenyl)-3-pyridylmethyl-aminomethyl]-chromane hydrochloride.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore, the invention relates to the use for the manufacture of a medicament for the treatment of adverse effects of anti-Parkinsonian drugs in idiopathic Parkinson's disease in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of adverse effects of anti-Parkinsonian drugs in idiopathic Parkinson's disease.

Furthermore, the present invention relates to the use of (R)-(−)-2-[5-(4-fluorophenyl)-3-pyridylmethylaminomethyl]-chromane or a physiologically acceptable salt thereof, for the manufacture of a medicament for the treatment of idiopathic Parkinson's disease.

A typical animal model for idiopathic Parkinson's disease is the Parkinsonian cynomolgus monkey according to P. J. Blanchet et al., Exp. Neurology 1998; 153: 214-222. Monkeys render parkinsonian by repeated injections of 1-methyl-4-phenyl-1,2,3,6-tetrahydropyridine (MPTP). Parkinsonian symptoms are qualitatively assessed by the use of the Laval University Disability Scale (B. Gomez-Mancilla et al., 1993; Mov. Disord. 8: 144-150) measuring the following symptoms: posture, mobility, climbing, gait, holding food, vocalizing, grooming, social interaction. (R)-(−)-2-[5-(4-fluorophenyl)-3-pyridyl-methyl-amino-methyl]-chromane reduced all the parkinsonian symptoms and increased total activity.

A typical study to investigate the efficacy of the compounds according to the invention in the treatment of idiopathic Parkinson's disease is described in the following. 180 patients of either sex with idiopathic Parkinson's disease participate in a double-blind study. The main inclusion criteria are Hoehn & Yahr stage $\geq 2.0$ (Hoehn H. M. et al, Neurology 1967; 17: 427-442), aged 50-80 years, symptom duration of at least 5 years. (R)-(−)-2-[5-(4-fluoro-phenyl)-3-pyridyl-methyl-aminomethyl]-chromane hydrochloride or placebo is administered as "add on" to the conventional Parkinson treatment, which is maintained unchanged during the whole study. The dose of blinded medication is titrated over a period of 4 weeks in a range from 2.5 to 10 mg b.i.d. Then the medication is kept constant for 1 week. Before the start of titration, at the end of the treatment period and 2 weeks after the end of the tiration period an assessment is performed in each patients using the unified Parkinson's disease rating scale (UPDRS part I to V according to S. Fahn et al., in: Recent developments in Parkinson's disease, vol. 2, MacMillan health information 1987, 153-163). This allows to detect simultaneously a beneficial effect of (R)-(−)-2-[5-(4-fluorophenyl)-3-pyridylmethyl-aminomethyl]-chromane or a physiologically acceptable salt thereof, in particular of (R)-(−)-2-[5-(4-fluorophenyl)-3-pyridylmethyl-aminomethyl]-chromane hydrochloride, on the global motoric function, on dystonia, motor fluctuations, and on psychosis. Furthermore, the efficacy to treat tremor is shown by the means of the UPDRS. The statistical analysis of the UPDRS scores demonstrates a significant clinical improvement under treatment with (R)-(−)-2-[5-(4-fluoro-phenyl)-3-pyridylmethyl-aminomethyl]-chromane hydrochloride.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore the invention relates to the use for the manufacture of a medicament for the treatment of idiopathic Parkinson's disease in which the physiologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of idiopathic Parkinson's disease.

The limiting factor of Parkinson treatment with I-dopa and/or dopamine agonists is often the occurrence of psychosis or dyskinesia and other motor fluctuations.

It has been found that (R)-(−)-2-[5-(4-fluorophenyl)-3-pyridylmethylaminomethyl]-chromane or a physiologically acceptable salt thereof enhance the anti-Parkinsonian effect of anti-Parkinsonian drugs as defined above without inducing extrapyramidal side effects.

Therefore, the add-on therapy with (R)-(−)-2-[5-(4-fluorophenyl)-3-pyridylmethyl-aminomethyl]-chromane or a physiologically acceptable salt thereof, in particular of (R)-(−)-2-[5-(4-fluorophenyl)-3-pyridylmethylaminomethyl]-chromane hydrochloride, now opens the possibility to increase the doses of I-dopa and/or dopamine agonists and/or all other anti-Parkinsonian drugs as defined above in order to counteract periods of insufficient motility ("off" phases) without provoking the above mentioned side effects. That represents an entirely novel approach in the treatment of Parkinson's disease leading to a significant benefit for the patients.

Thus, the invention relates to a pharmaceutical composition comprising, as active principles, (i) (R)-(−)-2-[5-(4-fluorophenyl)-3-pyridylmethylaminomethyl]-chromane or a physiologically acceptable salt thereof, and (ii) at least one anti-Parkinsonian drug, in combination with one or more pharmaceutically acceptable excipients.

Particularly, the invention relates to a pharmaceutical composition comprising, as active principles, (i) (R)-(−)-2-[5-(4-fluorophenyl)-3-pyridylmethyl-aminomethyl]-chromane hydrochloride, and (ii) I-dopa or I-dopa combined with benserazide or carbidopa, in combination with one or more pharmaceutically acceptable excipients.

The ratios of the respective amounts of (R)-(−)-2-[5-(4-fluorophenyl)-3-pyridylmethyl-aminomethyl]-chromane or one of its physiologically acceptable salts and of the conventional anti-Parkinsonian drug thus vary in consequences.

Preferably, the weight ratio of (R)-(−)-2-[5-(4-fluorophenyl)-3-pyridylmethylaminomethyl]-chromane or one of its physiologically acceptable salts to the conventional anti-Parkinsonian drug ranges from 1:1 to 1:100, preferably from 1:10 to 1:90 and better still from 1:40 to 1:60.

Another subject of the present invention is additionally the use of (R)-(−)-2-[5-(4-fluorophenyl)-3-pyridylmethyl-aminomethyl]-chromane or one of its physiologically acceptable salts in combination with at least one anti-Parkinsonian drug, for the preparation of a medicinal combination intended to enhance the anti-Parkinsonian effect of said anti-Parkinsonian drugs.

According to the invention, the term "medicinal combination" is intended to refer either to a pharmaceutical composition as defined above, in which the two active principles or compounds are the essential constituents of the same composition, or to a kit comprising two separate compositions, the first comprising (R)-(−)-2-[5-(4-fluorophenyl)-3-pyridylmethyl-aminomethyl]-chromane or one of its physiologically acceptable salts as sole active principle, and the second comprising at least one anti-Parkinsonian drug as active compound.

When the medicinal combination is in the form of a kit, the administration of the two compositions constituting this kit, although carried out separately, is simultaneous for a combined therapy. It is preferred to use (R)-(−)-2-[5-(4-fluorophenyl)-3-pyridylmethyl-aminomethyl]-chromane in the form of the hydrochloride.

Adverse effects of anti-Parkinsonian drugs as defined above are additionally known in particular in Parkinson syndromes.

Parkinson syndromes are e.g. multiple system atrophies (MSA), Steele-Richardson-Olszewski syndrome (=progressive supranuclear palsy), cortico-basal degeneration, olivoponto cerebellar atrophy or Shy Drager syndrome.

(R)-(−)-2-[5-(4-fluorophenyl)-3-pyridylmethylaminomethyl]-chromane or a physiologically acceptable salt thereof are useful for the treatment of Parkinson syndromes in particular of multiple system atrophies.

Therefore the present invention relates to the use of (R)-(−)-2-[5-(4-fluorophenyl)-3-pyridylmethylaminomethyl]-chromane or a physiologically acceptable salt thereof, for the manufacture of a medicament for the treatment of adverse effects in Parkinson syndromes.

The present invention relates additionally to the use of (R)-(−)-2-[5-(4-fluorophenyl)-3-pyridylmethylaminomethyl]-chromane or a physiologically acceptable salt thereof, for the manufacture of a medicament for the treatment of Parkinson syndromes.

A typical animal model is the reserpinized rat or mouse (e.g. M. S. Starr and B. S. Starr, J. Neural Transm.—Park. Dis. Dement. Sect., 1994; 7: 133-142; M. Gossel et al., J. Neural Transm.—Park. Dis. Dement. Sect., 1995; 10: 27-39; N. R. Hughes et al., Mov. Disord., 1998; 13: 228-233). Reserpine is a potent depleter of monoamines and produces nearly complete akinesia in both species. Prominent 24 h after application, the distance traveled and the time active is nearly zero as measured in conventional activity meters. (R)-(−)-2-[5-(4-fluorophenyl)-3-pyridylmethylaminomethyl]-chromane or a pharmaceutically acceptable salt thereof dose-dependently reduced akinesia, i.e. restored distance traveled and time active to about the level of normal animals.

Another more recent animal model is the striatonigral degeneration approach in the rat according to G. K. Wenning et al., J. Neural Transm. Suppl., 1999; 55: 103-113. Rats receive an unilateral injection of 6-hydroxydopamine into the left medial forebrain bundle followed by an injection of quinolinic acid into the ipsilateral striatum inducing nigrostriatal degeneration. The degeneration results in turning behavior to a challenge with dopaminomimetics such as apomorphine or amphetamine. Turning behavior is measured by an automated recorder. Turning behavior induced by apomorphine or amphetamine was dose-dependently antagonized by (R)-(−)-2-[5-(4-fluorophenyl)-3-pyridylmethylaminomethyl]-chromane or a pharmaceutically acceptable salt thereof.

Multiple system atrophy (MSA) is due to an expansive neurodegeneration in the extrapyramidal and autonomic nervous system which leads to an akinetic Parkinsonian syndrome with vegetative disturbances. In contrast to idiopathic Parkinson's disease the density of central dopamine receptors is markedly decreased and therefore, MSA patients poorly respond to dopaminergic drugs. Since (R)-(−)-2-[5-(4-fluorophenyl)-3-pyridylmethylaminomethyl]-chromane or a pharmaceutically acceptable salt thereof act predominantly via serotonin receptors on the extrapyramidal system, they are able to improve the motor performance in these otherwise mostly untreatable patients.

A typical study to investigate the efficacy of the compounds according to the invention in MSA patients encompasses 30 patients of either sex with a symptom duration of at least 5 years and a significant reduction of central dopamine receptors in positron emission tomography (PET) scan. The study design is similar to that described above for Parkinson's disease. (R)-(−)-2-[5-(4-fluorophenyl)-3-pyridylmethylaminomethyl]-chromane hydrochloride or placebo is titrated as "add on" to the conventional treatment (dose range 2.5 to 20 mg b.i.d.). Before the start of titration and at the end of the treatment period a complete UPDRS assessment is performed in each patient (primary outcome measure). After a 2-week wash-out period the two study arms are crossed over and the protocol is repeated. Statistical analysis of UPDRS demonstrates a significant clinical improvement under treatment with (R)-(−)-2-[5-(4-fluorophenyl)-3-pyridylmethyl-aminomethyl]-chromane hydrochloride.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore, the invention relates to the use for the manufacture of a medicament for the treatment of adverse effects of anti-Parkinsonian drugs in Parkinson syndromes in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of adverse effects of anti-Parkinsonian drugs in Parkinson syndromes.

Therefore, the invention relates to the use for the manufacture of a medicament for the treatment of Parkinson syndromes in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of Parkinson syndromes.

The present invention relates to the use of (R)-(−)-2-[5-(4-fluorophenyl)-3-pyridylmethylaminomethyl]-chromane or a physiologically acceptable salt thereof, for the manufacture of a medicament for the treatment of dyskinetic and/or choreatic syndromes.

Dyskinetic and/or choreatic syndromes are e.g. Huntington's disease, minor chorea or chorea of pregnancy.

(R)-(−)-2-[5-(4-fluorophenyl)-3-pyridylmethylaminomethyl]-chromane or a physiologically acceptable salt thereof are in particular useful for the treatment of Huntington's disease.

A typical animal model is the systemic 3-nitropropionic acid (3-NP) model in rats according to C. V. Borlongan et al., Brain Res., 1995; 697: 254-257.

Rats are treated with injections of the selective striatal neurotoxin 3-NP i.p. every fourth day (C. V. Borlongan et al., Brain Res. Protocols, 1997; 1: 253-257). After two injections of 3-NP, rats display nocturnal hyperactivity reflecting symptoms of early Huntington's disease, whereas rats treated with four injections of 3-NP display nocturnal akinesia (hypoactivity) reflecting symptoms of late Huntington's disease. Nocturnal activity is automatically measured in conventional activity cages by infrared beams. (R)-(−)-2-[5-(4-fluoro-phenyl)-3-pyridyl-methyl-amino-methyl]-chromane or a pharmaceutical acceptable salt thereof reduced both the nocturnal hyperactivity and akinesia.

A typical trial to establish the effect of the compounds according to the invention on chorea, voluntary motor performance, and functional disability in patients with Huntington's disease encompasses 32 genetically diagnosed patients. (R)-(−)-2-[5-(4-fluorophenyl)-3-pyridylmethylaminomethyl]-chromane hydrochloride or placebo is administered as "add on" to the conventional treatment, which is maintained unchanged during the whole study. The dose of blinded medication is titrated over a period of 3 weeks in a range from 2.5 to 20 mg b.i.d. Then the medication is held constant for 1 week. Assessments are performed in the week before and at the last day of the trial. Chorea is scored using the abnormal involuntary movement scale (AIMS, W. Guy, in: ECDEU assessment manual. Rockville Md.: US dept. of health, education and welfare, 1976: 534-537), the unified Huntington's disease rating scale (UHDRS, Huntington study group, 1996, Movement Disord, 11: 136-42), and judgement of video recordings. Voluntary motor performance is assessed using the UHDRS motor scale. Patients and their partners complete a questionnaire regarding functional disability. Statistical analysis demonstrates significant improvement of voluntary and involuntary motor performance in Huntington patients under treatment with (R)-(−)-2-[5-(4-fluorophenyl)-3-pyridylmethylaminomethyl]-chromane or a physiologically acceptable salt thereof.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore, the invention relates to the use for the manufacture of a medicament for the treatment of dyskinetic and/or choreatic syndromes, in particular for the treatment of Huntington's disease, in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of dyskinetic and/or choreatic syndromes.

The present invention relates to the use of (R)-(−)-2-[5-(4-fluorophenyl)-3-pyridylmethylaminomethyl]-chromane or a physiologically acceptable salt thereof, for the manufacture of a medicament for the treatment of dystonic syndromes.

Dystonic syndromes are e.g. spasmalic torticollis, writer's cramp, blepharospasm, Meige syndrome or dopasensitive dystonia. (R)-(−)-2-[5-(4-fluorophenyl)-3-pyridylmethylaminomethyl]-chromane or a physiologically acceptable salt thereof is in particular useful for the treatment of spasmalic torticollis and/or blepharospasm.

A typical animal model is the mutant dystonic hamster according to A. Richter and W. Löscher, Prog. Neurobiol. 1998; 54: 633-677. In this genetically dystonic hamsters, dystonic attacks are provoked by taking the animal from the home cage and placing it on a balance. The dystonic syndrome consists of a sequence of abnormal movements, and the severity of the single symptoms is rated by a scoring system. (R)-(−)-2-[5-(4-fluoro-phenyl)-3-pyridyl-methyl-amino-methyl]-chromane or a pharmaceutically acceptable salt thereof dose-dependently reduced the severity of dystonic symptoms.

To demonstrate the efficacy of the compounds according to the invention in dystonic syndromes, a double-blind, placebo-controlled study is performed in patients with cervical dystonia (spasmodic torticollis) who do not tolerate injection of botulinum toxin. (R)-(−)-2-[5-(4-fluorophenyl)-3-pyridylmethylaminomethyl]-chromane hydrochloride is titrated as described above in the range from 2.5 mg to 20 mg b.i.d. The Toronto western spasmodic torticollis rating scale (TWSTRS, C. L. Comella et al., 1997, Movement Disord, 12: 570-575) is used as primary outcome measure. A significant improvement in the TWSTRS scores is noted for the patients treated with (R)-(−)-2-[5-(4-fluorophenyl)-3-pyridylmethylaminomethyl]-chromane or one of its pharmaceutically acceptable salts.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore the invention relates to the use for the manufacture of a medicament for the treatment of dystonic syndromes, in particular of spasmalic torticollis and/or blepharospasm, in which the pharmacologically acceptable salt is (R)-(−)-2-[5-(4-fluorophenyl)-3-pyridylmethylaminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of dystonic syndromes.

The present invention relates to the use of (R)-(−)-2-[5-(4-fluorophenyl)-3-pyridylmethylaminomethyl]-chromane or a physiologically acceptable salt thereof, for the manufacture of a medicament for the treatment of extrapyramidal symptoms induced by neuroleptics.

Extrapyramidal motoric disturbances induced by neuroleptics are e.g. early dyskinesia, dystonia, akathisia, parkinsonoid, in particular bradykinesia, or tardive dyskinesia.

(R)-(−)-2-[5-(4-fluorophenyl)-3-pyridylmethylaminomethyl]-chromane or a physiologically acceptable salt thereof are useful particularly for the treatment of akathisia and/or tardive dyskinesia and/or parkinsonoid.

A typical animal model is neuroleptics-induced muscle rigidity in rats according to S. Wolfarth et al., Arch. Pharmacol. 1992; 345: 209-212. Rats are challenged with the conventional neuroleptic drug haloperidol which enhances muscle tone. Muscle tone is electromechanically measured as the resistance to passive flexion and extension of the hind limb. (R)-(−)-2-[5-(4-fluoro-phenyl)-3-pyridyl-methyl-amino-methyl]-chromane or a pharmaceutically acceptable salt thereof decreased the muscle tone enhanced by haloperidol.

Another typical animal model is the neuroleptics sensitized monkey according to D. E. Casey, Psychopharmacology, 1996; 124: 134-140. Monkeys treated repeatedly with conventional neuroleptics are highly sensitive to a subsequent challenge dose of neuroleptic drugs. When challenged, the monkeys immediately show extrapyramidal motor side effects such as dystonia, dyskinesias, akathisia, and bradykinesia which are rated by a scoring system. The conventional neuroleptic drug haloperidol is given as a challenge. When the before-mentioned extrapyramidal motor side effects occur, (R)-(−)-2-[5-(4-fluoro-phenyl)-3-pyridyl-methyl-amino-methyl]-chromane or a pharmaceutically acceptable salt thereof is administered; (R)-(−)-2-[5-(4-fluoro-phenyl)-3-pyridyl-methylamino-methyl]-chromane dose-dependently reduced the extrapyramidal motor side effects.

Tardive dyskinesia is a common adverse effect of long-term treatment with neuroleptics. A typical study to investigate the efficacy of the compounds according to the invention in tardive dyskinesia is described in the following. 32 schizophrenic (DSM-III-R) inpatients aged 25-60 years on long-term stable antipsychotic treatment (duration of at least 5 years) entered the study. (R)-(−)-2-[5-(4-fluorophenyl)-3-pyridylmethyl-aminomethyl]-chromane hydrochloride or placebo is administered as "add on" to the antipsychotic treatment, which is kept constant during the whole study. The dose of blinded medication is titrated over a period of 3 weeks in a range from 2.5 to 20 mg b.i.d. Then the medication is maintained under double-blind conditions for 2 weeks. After a 2-week wash-out period, the test drugs are crossed over. Assessments of tardive dyskinesia by means of the Abnormal Involuntary Movement Scale (AIMS, see above) and of Parkinsonian extrapyramidal side effects (UPDRS, see above) are made pretreatment and posttreatment. AIMS scores during treatment with (R)-(−)-2-[5-(4-fluorophenyl)-3-pyridyl-methyl-aminomethyl]-chromane hydrochloride are significantly lower than during placebo period.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore the invention relates to the use for the manufacture of a medicament for the treatment of extrapyramidal symptoms induced by neuroleptics, in particular of akathisia and/or tardive dyskinesia, in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of extrapyramidal symptoms induced by neuroleptics.

The present invention relates to the use of (R)-(−)-2-[5-(4-fluorophenyl)-3-pyridylmethylaminomethyl]-chromane or a physiologically acceptable salt thereof, for the manufacture of a medicament for the treatment of tremor.

Tremor includes all types of tremors such as essential tremor, activated physiological tremor, cerebellar tremor, orthostatic tremor or drug-induced tremor.

(R)-(−)-2-[5-(4-fluorophenyl)-3-pyridylmethylaminomethyl]-chromane or a physiologically acceptable salt thereof are particularly useful for the treatment of essential tremor and/or drug-induced tremor.

Typical animal models utilize either genetic mutant animals or are models where tremor is induced by a pharmacological agent (for review: H. Wilms et al., Mov. Disord., 1999; 14: 557-571).

Typical genetic models in mutant animals are the Campus Syndrome in the Pietrain pig according to A. Richter et al. (Exp. Neurology, 1995; 134: 205-213) or the Weaver mutant mouse according to J. R. Simon and B. Ghetti (Mol. Neurobiol., 1994; 9: 183-189). In the Campus Syndrome model, these mutant pigs show a high-frequency tremor when standing and during locomotion, but not while lying at rest. Assessment of tremor is made by accelerometric recording. In the Weaver mutant mouse, degenerative cerebellar atrophy is fould in association with tremor, gait instability, and toppling over the sides after a few steps. Gait disability and toppling result in dramatically reduced locomotor activity measured by the distance traveled and the time spent with ambulation in conventional activity cages.

(R)-(−)-2-[5-(4-fluoro-phenyl)-3-pyridyl-methyl-amino-methyl]-chromane or one of its pharmaceutically acceptable salts improved the Campus Syndrome in the Pietrain pig, i.e. reduced disabling tremor when standing and during locomotion, and enhanced locomotor activity in the Weaver mutant mouse.

A typical animal model for drug-induced tremors is the oxotremorine-induced tremor (e.g. H. Hallberg and O. Almgren, Acta Physiol. Scand., 1987; 129: 407-13; J. G. Clement and W. R. Dyck, J. Pharmacol. Meth., 1989; 22: 25-36). Oxotremorine induces tremor which is measured by a rating scale. (R)-(−)-2-[5-(4-fluoro-phenyl)-3-pyridyl-methyl-amino-methyl]-chromane or one of its pharmaceutically acceptable salt inhibited oxotremorine-induced tremors.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore the invention relates to the use for the manufacture of a medicament for the treatment of tremors, in particular of essential tremors and/or drug-induced tremors, in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of tremor.

The present invention relates to the use of (R)-(−)-2-[5-(4-fluorophenyl)-3-pyridylmethylaminomethyl]-chromane or a physiologically acceptable salt thereof, for the manufacture of a medicament for the treatment of extrapyramidal movement disorders chosen from the group consisting of Gilles de la Tourette syndrome, ballism, myoclonus, restless legs syndrome and Wilson's disease.

A typical animal model for myoclonus is myoclonus induced by an acute hypoxic episode according to D. D. Truong et al., Mov. Disord., 1994; 9: 201-206). In this model of posthypoxic myoclonus, rats undergo a cardiac arrest for 8 minutes and are resuscitated thereafter. Myoclonic jerks occur spontaneously but can be provoked by auditory stimulation, too, worsening over the days following cardiac arrest. (R)-(−)-2-[5-(4-fluoro-phenyl)-3-pyridyl-methyl-amino-methyl]-chromane or one of its pharmacologically acceptable salts dose-dependently reduced the number of spontaneous and auditory-evoked myoclonic jerks.

A preferred salt of (R)-(−)-2-[5-(4-fluorophenyl)-3-pyridylmethylaminomethyl]-chromane is (R)-(−)-2-[5-(4-fluorophenyl)-3-pyridylmethylaminomethyl]-chromane hydrochloride.

Therefore the invention relates to the use for the manufacture of a medicament for the treatment of extrapyramidal movement disorders chosen from the group consisting of Gilles de la Tourette syndrome, ballism, myoclonus, restless legs syndrome and Wilson's disease in which the pharmacologically acceptable salt is (R)-(−)-2-[5-(4-fluorophenyl)-3-pyridylmethyl-aminomethyl]-chromane hydrochloride.

Additionally, the invention relates to the use of a pharmaceutical composition containing at least one compound of (R)-(−)-2-[5-(4-fluorophenyl)-3-pyridylmethyl-aminomethyl]-chromane or one of its biocompatible salts together with at least one solid, liquid or semiliquid excipient or adjunct for the treatment of extrapyramidal movement disorders chosen from the group consisting of Gilles de la Tourette syndrome, ballism, myoclonus, restless legs syndrome and Wilson's disease.

The extrapyramidal movement disorders such as Steele-Richardson-Olszewski syndrome (=progressive supranuclear palsy), cortico-basal degeneration, olivo-ponto cerebellar atrophy, Shy Drager syndrome, minor chorea, chorea of pregnancy, writer's cramp, blepharospasm, Meige syndrome, dopa-sensitive dystonia, Gilles de la Tourette syndrome, ballism, myoclonus, restless legs syndrome, and Wilson's disease are not frequent enough to perform regular double-blind trials. However, the medical need in this field is pressing since no sufficient therapies are available so far.

Therefore, open-label observations in few selected patients are an adequate method to demonstrate the efficacy of (R)-(−)-2-[5-(4-fluorophenyl)-3-pyridylmethyl-aminomethyl]-chromane or a physiologically acceptable salt thereof.

All the pharmaceutical preparations used for the treatment of extrapyramidal movement disorders and/or for the treatment of adverse effects of anti-Parkinsonian drugs in extrapyramidal movement disorders including the medicinal combination can be used as pharmaceuticals in human or veterinary medicine.

The compositions of the invention are preferably administered parenterally, or better still orally, although the other routes of administration, for instance such as rectal administration, are not excluded.

Suitable excipients are organic or inorganic substances which are suitable for enteral (e.g. oral), parenteral or topical administration and which do not react with (R)-(−)-2-[5-(4-fluorophenyl)-3-pyridylmethyl-aminomethyl]-chromane and/or one of its biocompatible salts, for example water, vegetable oils, benzyl alcohols, alkylene glycols, polyethylene glycols, glycerol triacetate, gelatine, carbohydrates such as lactose or starch, magnesium stearate, talc, petroleum jelly. Forms which are used for oral administration are, in particular, tablets, pills, sugar-coated tablets, capsules, powders, granules, syrups, liquids or drops, forms for rectal administration are, in particular suppositories, forms for parenteral administration are, in particular, solvents, preferably oily or aqueous solutions, furthermore suspensions, emulsions or implants, and forms for topical administration are transdermal plasters, ointments, creams or powders. 1-[4-(5-cyanoindol-3-yl)butyl]-4-(2-carbamoyl-benzofuran-5-yl)-piperazine and/or one of its pharmaceutically acceptable salts may also be lyophilized and the resulting lyophilisates used for example for the preparation of injectable products. The abovementioned preparations can be in sterilized form and/or comprise auxiliaries such as glidants, preservatives, stabilizers and/or wetting agents, emulsifiers, salts for modifying the osmotic pressure, buffer substances, colourings, flavourings and/or other active ingredients, e.g. one or more vitamins.

Preparations may, if desired, be designed to give slow release of (R)-(−)-2-[5-(4-fluorophenyl)-3-pyridylmethylaminomethyl]-chromane or a biocompatible salt thereof.

The examples which follow relate to pharmaceutical products:

EXAMPLE A

Vials

A solution of 100 g of (R)-(−)-2-[5-(4-fluorophenyl)-3-pyridylmethylaminomethyl]-chromane or a physiologically acceptable salt thereof and 5 g of disodium hydrogen phosphate in 3 l of twice-distilled water is brought to pH 6.5 with 2N hydrochloric acid, filter-sterilized, filled into vials, lyophilized under sterile conditions and sealed in sterile form. Each vial comprises 5 mg of active ingredient.

EXAMPLE B

Suppositories

A mixture of 20 g of (R)-(−)-2-[5-(4-fluorophenyl)-3-pyridylmethylaminomethyl]-chromane or a physiologically acceptable salt thereof is melted with 100 g of soya lecithin and 1400 g of cocoa butter, and the mixture is poured into moulds and left to cool. Each suppository comprises 20 mg of active ingredient.

EXAMPLE C

Solution

A solution is prepared from 1 g of (R)-(−)-2-[5-(4-fluorophenyl)-3-pyridylmethyl-aminomethyl]-chromane or a physiologically acceptable salt thereof, 9.38 g of $NaH_2PO_4.2H_2O$, 28.48 g of $Na_2HPO_4.12H_2O$ and 0.1 g of benzalkonium chloride in 940 ml of twice-distilled water. The pH is brought to 6.8, and the solution is made up to 1 l and sterilized by irradiation. This solution can be used in the form of eyedrops.

EXAMPLE D

Ointment 500 mg of (R)-(−)-2-[5-(4-fluorophenyl)-3-pyridylmethylaminomethyl]-chromane or a physiologically acceptable salt thereof are mixed with 99.5 g of petroleum jelly under aseptic conditions.

EXAMPLE E-1

Tablets

A mixture of 1 kg of (R)-(−)-2-[5-(4-fluorophenyl)-3-pyridylmethylaminomethyl]-chromane or a physiologically acceptable salt thereof, 4 kg of lactose, 1.2 kg of potato starch, 0.2 kg of talc and 0.1 kg of magnesium stearate is tableted in the customary manner in such a way that each tablet comprises 10 mg of active ingredient.

EXAMPLE E-2

Tablets

A mixture of 20 g of (R)-(−)-2-[5-(4-fluorophenyl)-3-pyridylmethylaminomethyl]-chromane hydrochloride, 1 kg of I-dopa, 250 g benserazide, 4 kg of lactose, 1.6 kg of potato starch, 0.2 kg of talc and 0.1 kg of magnesium stearate is tableted in the customary manner in such a way that each tablet comprises 0.2 mg (R)-(−)-2-[5-(4-fluorophenyl)-3-pyridylmethyl-aminomethyl]-chromane hydrochloride, 10 mg of l-dopa and 2.5 mg benserazide.

EXAMPLE F

Sugar-Coated Tablets

A mixture is tableted analogously to Example E, and the tablets are subsequently coated in the customary manner with a coating of sucrose, potato starch, talc, tragacanth and colouring.

EXAMPLE G

Capsules 2 kg of (R)-(−)-2-[5-(4-fluorophenyl)-3-pyridylmethyl-aminomethyl]-chromane or a physiologically acceptable salt thereof are filled into hard gelatin capsules in the customary manner so that each capsule comprises 20 mg of the active ingredient.

EXAMPLE H

Ampoules

A solution of 1 kg of (R)-(−)-2-[5-(4-fluorophenyl)-3-pyridylmethylaminomethyl]-chromane or a physiologically acceptable salt thereof in 60 l of twice-distilled water is filter-sterilized, filled into ampoules, lyophilized under sterile conditions and sealed in sterile form. Each ampoule comprises 10 mg of active ingredient.

EXAMPLE I

Spray for Inhalation 14 g of (R)-(−)-2-[5-(4-fluorophenyl)-3-pyridylmethyl-aminomethyl]-chromane or a physiologically acceptable salt thereof are dissolved in 10 l of isotonic NaCl solution, and the solution is filled into commercially available pump-operated spray containers. The solution can be sprayed into mouth or nose. One actuation (approximately 0.1 ml) corresponds to a dose of approximately 0.14 mg.

The invention claimed is:

1. A method for treating an adverse effect of an anti-Parkinsonian drug administered to a patient with idiopathic Parkinson's disease comprising administering to said patient a pharmaceutical composition comprising an effective amount of (R)-(−)-2-[5-(4-fluorophenyl)-3-pyridylmethylaminomethyl]-chromane or a physiologically acceptable salt thereof, and a pharmaceutically acceptable carrier, wherein the adverse effect of said anti-Parkinsonian drug is an extrapyramidal movement disorder, which is motor fluctuations.

2. A method for treating an adverse effect of an anti-Parkinsonian drug administered to a patient with idiopathic Parkinson's disease comprising administering to said patient a pharmaceutical composition comprising an effective amount of (R)-(−)-2-[5-(4-fluorophenyl)-3-pyridylmethylaminomethyl]-chromane or a physiologically acceptable salt thereof, and a pharmaceutically acceptable carrier, wherein the adverse effect of said anti-Parkinsonian drug is an extrapyramidal movement disorder, which is dyskinesia.

3. A method according to claim 2, wherein the dyskinesia is levodopa-induced dyskinesia in Parkinson's disease.

4. A method according to claim 2, wherein the dyskinesia is treatment-associated dyskinesia in Parkinson's disease.

5. A method according to claim 2, wherein the anti-Parkinsonian drug is L-Dopa.

6. A method according to claim 3, wherein the anti-Parkinsonian drug is L-Dopa.

7. A method according to claim 4, wherein the anti-Parkinsonian drug is L-Dopa.

* * * * *